United States Patent
Shah et al.

(10) Patent No.: US 11,284,816 B2
(45) Date of Patent: Mar. 29, 2022

(54) MULTI-ANALYTE CONTINUOUS GLUCOSE MONITORING

(71) Applicant: PercuSense, Inc., Valencia, CA (US)

(72) Inventors: Rajiv Shah, Rancho Palos Verdes, CA (US); Bradley C Liang, Bloomfield Hills, MI (US); Ellen Bowman, Pasadena, CA (US); Katherine Wolfe, Mississauga (CA)

(73) Assignee: PercuSense, Inc., Valencia, CA (US)

( * ) Notice: Subject to any disclaimer, the term of this patent is extended or adjusted under 35 U.S.C. 154(b) by 219 days.

(21) Appl. No.: 16/273,920

(22) Filed: Feb. 12, 2019

(65) Prior Publication Data

US 2019/0246962 A1    Aug. 15, 2019

Related U.S. Application Data

(60) Provisional application No. 62/630,101, filed on Feb. 13, 2018.

(51) Int. Cl.
| | |
|---|---|
| *A61B 5/145* | (2006.01) |
| *A61B 5/1473* | (2006.01) |
| *A61B 5/1495* | (2006.01) |
| *A61B 5/1486* | (2006.01) |

(52) U.S. Cl.
CPC ........ *A61B 5/14532* (2013.01); *A61B 5/1473* (2013.01); *A61B 5/14542* (2013.01); *A61B 5/14546* (2013.01); *A61B 5/1495* (2013.01); *A61B 5/14503* (2013.01); *A61B 5/14865* (2013.01)

(58) Field of Classification Search
CPC . A61B 5/14532; A61B 5/7275; A61B 5/7282; A61B 5/14546; A61B 5/7285; A61B 5/1473; A61B 5/14865; A61B 5/14542; A61B 5/14503
See application file for complete search history.

(56) References Cited

U.S. PATENT DOCUMENTS

| | | | |
|---|---|---|---|
| 2005/0065556 A1* | 3/2005 | Reghabi | A61B 5/02055 607/5 |
| 2009/0178935 A1* | 7/2009 | Reymond | G01N 27/3273 205/777.5 |
| 2012/0265034 A1* | 10/2012 | Wisniewski | A61B 5/14532 600/309 |
| 2012/0296187 A1* | 11/2012 | Henning | A61B 5/14503 600/347 |
| 2013/0041242 A1* | 2/2013 | Karlsson | A61B 5/686 600/365 |

(Continued)

*Primary Examiner* — Eric F Winakur
*Assistant Examiner* — Abid A Mustansir
(74) *Attorney, Agent, or Firm* — PercuSense, Inc.

(57) ABSTRACT

A system to automatically detect at least one physiological state is disclosed. The system includes a single probe for insertion within a subject that has an analyte sensor array for continuous monitoring of at least glucose and a second analyte. The system further includes an electronics module that includes a power supply, a processor, memory and a bi-directional communications module. When the electronics module is coupled with the analyte sensor array the power supply delivers power to the analyte sensor array and the processor. The processor analyzing glucose and the second analyte data to detect a first physiological state from a plurality of physiological states.

15 Claims, 4 Drawing Sheets

(56) References Cited

U.S. PATENT DOCUMENTS

| 2015/0126835 A1* | 5/2015 | Mao | C12Q 1/002 |
| | | | 600/347 |
| 2016/0029966 A1* | 2/2016 | Salas-Boni | A61B 5/14532 |
| | | | 600/347 |

* cited by examiner

MULTI-ANALYTE CONTINUOUS GLUCOSE MONITORING

RELATED APPLICATIONS

This application claims the benefit of U.S. provisional application No. 62/630,101, filed Feb. 13, 2018. The application listed above are hereby incorporated by reference in their entireties for all purposes.

FIELD OF THE INVENTION

The invention generally relates to systems and methods for real time monitoring of physiological parameters to enable monitoring of physical conditions. More specifically, the invention relates to the use of sensors and related electronics in conjunction with algorithms and software to enable improved, partially automatic, or fully automatic closed loop control of physical conditions associated with chronic conditions such as, but not limited to diabetes.

BACKGROUND OF THE INVENTION

Diabetes is a growing healthcare crisis, affecting nearly 30 million people in the United States. Approximately 10 percent of those affected require intensive glucose and insulin management. In hospital patients, hypoglycemia in both diabetic and non-diabetic patients is associated with increased cost and short- and long-term mortality.

To prevent complications, diabetes requires ongoing management. Continuous glucose monitoring (CGM) has been shown in studies to be the most effective way to improve glucose control, whether used with insulin injections or a continuous insulin pump. Current commercially available closed loop solutions are challenged by everyday situations where insulin requirements change rapidly and often unpredictably. Augmenting continuous glucose monitoring (CGM) through measures that are sensitive and specific to behaviors associated with physiological states or conditions can enable insight into, and even predict changes in glucose and insulin dynamics that impact insulin delivery decisions. This insight can enable an improved automated or personalized solutions that result in better control, less burden and further adoption of CGM.

Accordingly, it would be highly advantageous to supplement glucose sensing with additional parameters that enable automated recognition of a behavior being performed or a physiological state being entered. The claimed invention seeks to address the use of a single probe inserted into a subject that is capable of real time measurements of multiple analytes. The interaction between the multiple analytes being used to recognize various physical behaviors or physiological states. In many examples discussed below multiple analytes and physical parameters are monitored with respect to diabetes. While embodiments and examples may be related to particular analytes and physical parameters, the scope of the disclosure and claims should not be construed to be limited to the specifically addressed analytes and parameters associated with diabetes. Rather it should be recognized that additional or other analytes and physical parameters can be monitored to assist in the detection and diagnosis of various metabolic conditions or general physiological health.

BRIEF SUMMARY OF THE INVENTION

In one embodiment, a system to automatically detect at least one physiological state is disclosed. The system includes a single probe for insertion within a subject that has an analyte sensor array for continuous monitoring of at least glucose and a second analyte. The system further includes an electronics module that includes a power supply, a processor, memory and a bi-directional communications module. When the electronics module is coupled with the analyte sensor array the power supply delivers power to the analyte sensor array and the processor. The processor analyzing glucose and the second analyte data to detect a first physiological state from a plurality of physiological states.

In another embodiment, a system to automatically detect a plurality of physiological states is disclosed. The system includes a single probe for insertion within a subject having an analyte sensor array for continuous monitoring of glucose, a second analyte, and a third analyte. The system further includes an electronics module having a power supply, a processor, memory, a bi-directional communications module, and physical sensor suite. The electronics module configured to couple with the analyte sensor array where the power supply powers the analyte sensor array and the processor. The processor analyzing data from the physical sensor suite, glucose, the second analyte, and the third analyte to detect a first physiological state or a second physiological state from a plurality of physiological states.

Other features and advantages of the invention will become apparent from the following detailed description, taken in conjunction with the accompanying drawings that illustrate, by way of example, various features of embodiments of the invention.

DETAILED DESCRIPTION

Automated insulin delivery (AID) technology has been successful in improving glucose control but has yet to deliver on the hope of fully automated closed loop control. Current AID systems deliver only basal insulin and use conservative glucose targets that perpetuate elevated HbA1c values without eliminating hypoglycemia. One embodiment of an ideal 24 hour, 7-days a week artificial pancreas (AP) system would control both basal and bolus insulin and enable users to achieve the American Diabetes Association recommendation of HbA1c less than 6.5% while eliminating severe hypoglycemia. To achieve this goal, the future of diabetes management through AID and AP systems will need to rely on multi-variable inputs.

Realizing the potential of AID systems involves advancing the degree of automation to include both basal and bolus insulin delivery through the inclusion of additional real-time signals. Augmenting continuous glucose monitoring (CGM) through measures that are sensitive and specific to behaviors such as meals, exercise, stress, and sleep provides insight into changes in glucose and insulin dynamics imparted by a subject's metabolic and physical activities. Multivariable automated pancreas (MAP) systems tested in academic and small scale clinical settings have demonstrated promise and demonstrate the validity of the approach. However, the challenge is that these systems derive physical signals associated with behaviors from other body-worn devices outside of the CGM device. The burden of wearing multiple devices couple with the challenges that exist monitoring physiological signals suggests limited widespread utility of currently envisioned MAP systems.

Discussed below is a multi-analyte continuous glucose monitor (MCGM) system that enables embodiments of MAP through the use of biochemical signals specific to physiological conditions such as, but not limited to meals, exercise, stress, and sleep. In some embodiments detection of physiological conditions is accomplished using a combination of biochemical signals and physical sensors. The contextual biochemical signals and optional physical signals are derived from the same minimally invasive probe producing a continuous glucose signal without increasing implant size. The ability to measure multiple biochemical signals via a single probe, combined with optional physical sensors in the same package results in a system that reduces burden on the subject rather than requiring mindfulness of multiple sensor insertions and separate physical sensors. The seamless integration of multiple signal streams enables 24-7 insulin delivery automation. It would also enable rapid individualization optimization efforts from the additional time series data generated and the knowledge that can be distilled from the interaction between signal streams.

Figure 1:
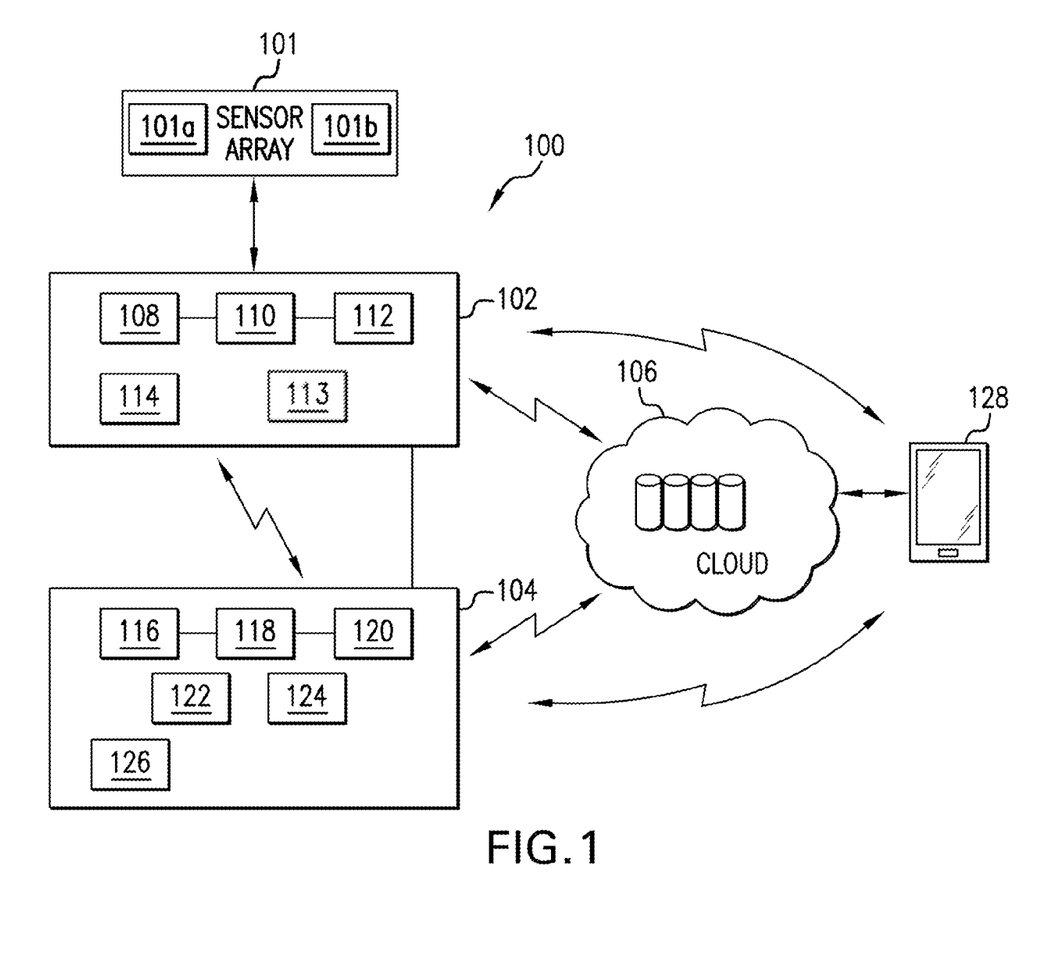
FIG. 1 is an exemplary block diagram showing components within a system to detect at least one physiological state.

FIG. 1 is an exemplary block diagram showing components within a system 100 to detect at least one physiological state, in accordance with embodiments of the invention. Broadly, the system 100 includes a sensor array 101 that includes analytes sensors 101$a$ and physical sensors 101$b$ powered by an electronics module 102. The electronic module 102 further enables bidirectional communication with a plurality of remote devices, such as, but not limited to an external monitor 104, cloud computing systems 106 and mobile devices 128. The remote devices enable different aspects of functionality of the system 100, such as, but not limited to entry of patient specific data, display of historical and trending data acquired by the system 100, and machine learning. The totality of components shown in FIG. 1 enable the system 100 to be used across a variety of environments such as ambulatory patient monitoring and remote monitoring. However, embodiments tailored for a specific environment may not include all of the components shown in FIG. 1. For example, use of the system 100 as an ambulatory remote monitor may not utilize an external monitor 104. Likewise, when the system 100 is used as a patient monitor in a hospital environment, the system 100 may not include a mobile device 128. The inclusion of all of the components within FIG. 1 is intended to illustrate the flexibility and adaptability of the system 100 to be used in different environments. However, regardless of environment, an element of the system 100 that is required for all embodiments is the sensor array 101.

Sensor Array

Figure 2A:
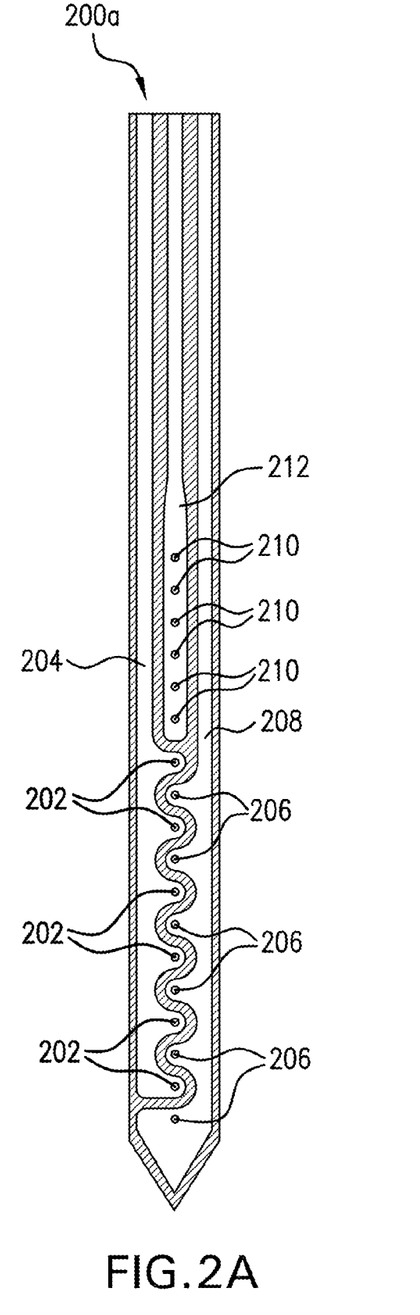
FIGS. 2A and 2B are exemplary views of an A-side and a B-side of an implantable probe, also referred to as an analyte sensor, within the sensor array.
Figure 2B:
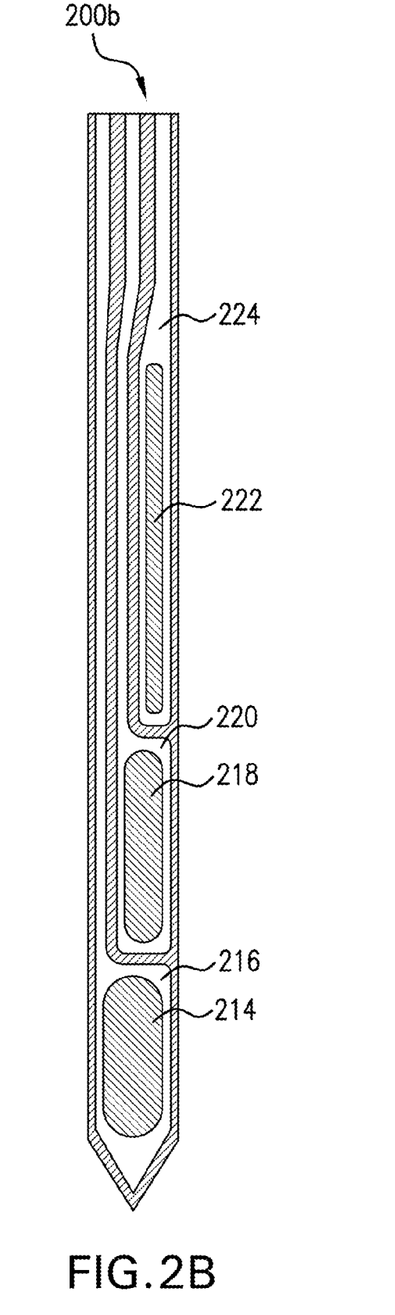

FIGS. 2A and 2B are exemplary views of an A-side 200$a$ and a B-side 200$b$ of an implantable probe, also referred to as an analyte sensor 101$a$, within the sensor array 101, in accordance with embodiments of the invention. In varying embodiments the sensor array 101 includes the analyte sensor 101$a$ having an A-side 200$a$ and a B-side 200$b$ that enables continuous detection of glucose and at least a second analyte. While some embodiments of the analyte sensor 101$a$ use both A-side and B-side, other embodiments utilize a single side. In addition to glucose, exemplary second analytes that can be measured on the A-side 200$a$, B-side 200$b$, or across both A-side and B-side, include, but are not limited to lactate, oxygen, ROS, ketones, and the like. While illustrated as a single probe, varying embodiments of the sensor array 101 include multiple probes, each capable of measuring identical or different analytes using different combinations of analyte sensors 101$a$. Examples of a sensor array 101 having multiple probes but a single point of entry can be found in combined sensing and infusion devices discussed in U.S. patent application Ser. No. 15/455,115 filed on Mar. 9, 2017 which is hereby incorporated for reference for all purposes. In some embodiments the analyte sensor 101$a$, or implantable probe, can be implanted via a surgical procedure. In other embodiments, the analyte sensor 101$a$ can be temporarily inserted into tissue, such as, but not limited to subcutaneous tissue, muscle tissue, organ tissue, or the like. In most embodiments, the implantable probe may be temporarily inserted into tissue for varying durations that can be measured in minutes, hours, days, weeks, or months. While many embodiments of the implantable probe, or analyte sensor 101$a$ have been discussed as using both an A-side 200$a$ and B-side 200$b$, other embodiments utilize a single side of the implantable probe. In these embodiments the requisite sensor elements are found either on a single side of the implantable probe and distributed across other sensor features within the sensor array.

FIG. 2A is a view of the A-side 200$a$ that includes first working electrodes 202 and second working electrodes 206 along with corresponding first electrode trace 204 and second electrode trace 208. In many embodiments the first working electrodes 202 are transducers configured to detect, or measure, glucose concentration. The second working electrodes 206 can be configured to measure the concentration of a second analytes such as, but not limited to lactate, oxygen, ROS, ketones or the like. FIG. 2B is a view of the B-side 200$b$ that includes a plurality of combination counter-reference electrodes 214 and 218 formed on electrode traces 216 and 220 respectively. In preferred embodiments a two-electrode system consisting of the first and second working electrodes with corresponding combined counter-reference electrodes, or pseudo-reference electrodes, are used to detect concentrations of the various analytes. However, other embodiments may use of a three-electrode system having a working electrode along with a counter electrode and a reference electrode.

FIGS. 2A and 2B further include optional third working electrodes 210 formed on third electrode trace 212 in addition to third counter-reference electrode 222 formed on electrode trace 224. In some embodiments the third working electrodes 210 can be duplicative of the second working electrodes 206, that is to say the third working electrodes 210 measure or detect the same analyte as the second working electrodes 206. However, in other embodiments, the third working electrodes 210 are used to measure a third analyte, that is to say the analyte sensor 101$a$ is capable of measuring glucose, and at least two of oxygen, lactate, ROS, ketones or the like. Common among the embodiments is at least measuring glucose because glucose measurements drive therapy decisions but can lack the ability to predict changing insulin dynamics. The addition of the second analyte and options third analyte are intended to supplement glucose and provide the ability to predict changing insulin dynamics.

The sensor array 101 further includes additional sensors or abilities to measure physical characteristics such as, but not limited to movement (via accelerometers), elapsed time, temperature, tissue impedance (such as tissue hydration levels), sensor hydration levels, and even electrocardiogram data via skin contacting electrodes. Measurement of some physical characteristics is enabled via physical sensors or other instrumentation incorporated within or on the electronics module. In many embodiments, detecting a physiological state is accomplished via a combination of the analyte sensors 101*a* implanted within the subject and the physical sensors 101*b* associated with the electronics module. The specific physical sensors discussed should not be construed as limiting. Other and additional physical characteristics from physical sensors associated with the sensor array 101 can be used as inputs to detect or confirm various physiological states. Monitoring hydration levels of at least one, some, or all of the transducers within the sensor array 101 enables detection of whether the sensor array 101 is properly implanted within desirable tissue. Additionally, monitoring the sensor elements for proper hydration can be used as a trigger to enable at least one of determining or detecting a physiological state, data recording, and/or data transmission.

Electrochemical impedance spectroscopy (EIS) applied across any electrode pair within the sensor array 101 can be used to measure or infer tissue impedance to determine tissue hydrations levels, or a fluid status within subcutaneous tissue of a subject being monitored. Utilizing the sensor array enables continuous monitoring of tissue impedance to detect changes in fluid content within the interstitial space. In some embodiments an EIS scan is across specific frequencies is used to correlate impedance with sodium concentrations within tissue surrounding the sensor via either a lookup table or via an equivalent circuit model. Regardless of how impedance is determined, real-time monitoring can enable EIS measurements over time to determine if there is and increase in fluid within interstitial fluid based on changes in salinity of the interstitial fluid. If salinity decreases, one can infer there is additional fluid build up. Conversely, if salinity increases, it can be inferred that the fluid level within the interstitial fluid is decreasing. Increased, or increasing fluid within interstitial fluid results in lower relative impedance, measurable across multiple frequencies.

Rapid changes in tissue impedance may be correlated with changes in hydration which can be correlated to detecting a physiological state such as, but not limited to sleep, exercise, strenuous exercise and meal intake. In some embodiments, fluid status or hydration of a subject contributes to detecting a physiological state because fluid status provides context and a normalizing factor for other measurements, such as, but not limited to tissue oxygen levels and concentrations of ROS. Absolute and trend information derived from tissue hydration levels enable adjustment or modifications to detecting a physiological state. In still other embodiments, tissue hydration levels enable additional insight regarding perfusion of analytes within different types of tissues. For example, in various embodiments tissue hydration levels for a sensor array 101 placed in muscle provides additional or less information than a sensor array 101 that is placed in adipose tissue.

In some embodiments data from a single analyte sensor (e.g., glucose) is combined with data from any one to all of the physical characteristic sensors to help detect a physiological state. In other embodiments multiple analytes measured from a single probe are used in conjunction with the data from any one to all of the physical characteristic sensors to detect a physiological state. The rationale for detecting physiological states based on less than every data stream from the sensor array is to enable tailoring of the sensor array to a particular environment. For example, if a patient is breathing with assistance of a ventilator or receiving oxygen via an oxygen mask, it may not be preferred to have a risk score factor in data acquired via the tissue oxygen sensor and ROS. Alternatively, when using a ventilator or using an oxygen mask it may be advantageous to include tissue oxygen and ROS in order to determine efficacy of therapy via expected or predicted changes in the microcirculation.

Detecting a physiological state is accomplished by analyzing real-time data from the sensor array 101 for trends in the data that are indicative of a physiological state. In some embodiments detecting a physiological state is based on data from the sensor array exceeding a threshold value. In some embodiments the threshold values for various physiological states are associated with data from only the analyte sensors 101*a*. In other embodiments, the threshold values for some physiological states are associated with data from the analyte sensors 101*a* and the physical sensors 101*b*. In still other embodiments threshold values for physiological states are set based on data from the physical sensors 101*b*. Threshold values can be associated with absolute changes or rates of change of a single analyte, multiple analytes with or without additional absolute changes or rates of change data from the physical sensors. In still other embodiments, detecting a physiological state is based on a change in data from the sensor array relative to historical data from the sensor array. Typical changes in data that may be detected include, but are not limited to, a change in value, rate, coefficient of variance.

Once a threshold value for a physiological state has been crossed, a probability of the physiological state can be determined. As additional data is acquired from the sensor array the probability of the physiological state is updated. Operating as a standalone continuous glucose monitoring system data associated with detection of a physiological state can be saved for later review in order to refine the detection algorithm. When used in conjunction with an artificial pancreas system the detection of a physiological state can be used to automatically adjust basal and bolus insulin delivery.

In many embodiments, the analyte sensor 101*a* is intended to be placed in subcutaneous tissue where the plurality of working electrodes within the sensor array 101 produce signals related to the analyte each transduced is configured to measure or detect (e.g., glucose, tissue oxygen, lactate, ROS, ketones). In embodiments where the analyte sensor is intended to be placed within subcutaneous tissue, the analyte sensor 101*a* may also be referred to as a probe. Placement within subcutaneous tissue enables a unique perspective for an oxygen sensor that is substantially different than common SpO2 oxygen measurements. Specifically, with embodiments of the analyte sensors 101*a*, oxygen within tissue is being measured rather than a measurement of SpO2 that is an estimation of arterial oxygen. When detecting a physiological state it is advantageous to measure oxygen within tissue rather than estimated arterial oxygen because oxygen within tissue is a direct measurement of oxygen perfusion. Tissue oxygen provides insight into exercise as tissue oxygen levels tend to decline with exercise. Identification of exercise via changes in tissue oxygen levels can automatically reduce, prevent or delay basal insulin delivery that could create a risk of serious hypoglycemia. Tissue oxygen can further provide insight to meal ingestion as there have been measurable increases in muscle oxygen consumption within 15 minutes after a meal. Changes in tissue oxygen further provide insight to when a subject sleeps, with some data indicating changes in oxygen concentrations offer more reliable detection of sleep than accelerometers.

In many embodiments the analyte sensors 101*a* include transducers configured to measure ROS. In some embodiments, a two-electrode system is employed where each of the working electrodes electrochemically measure a particular analyte relative to a counter electrode. In other embodiments, a three-electrode system is employed where each of the working electrodes electrochemically measure a particular analyte relative to a counter and reference electrode. In one embodiments, ROS would be enabled via a pair of electrodes. An ROS measurement can be acquired through a first pair of electrodes that includes a standard working electrode and a combined counter/reference electrode, or pseudo-reference electrode.

In preferred embodiments the ROS electrodes would provide calibration free, real-time concentration levels of oxidizing agents. In many embodiments ROS measurements may provide some insight into oxidative stress. It has been shown that ROS increases at times of stress and illness, both of which impact glucose and insulin dynamics. Additionally, oxidative stress has been demonstrated to impact the timing of postprandial glucose excursions, causing a delay in glucose decline after a meal. Because of the involvement of oxidative stress in many diabetes complications, concentrations of ROS can also provide information on the risk of developing secondary diseases.

In still other embodiments, the analyte sensors 101*a* include transducers configured to measure lactate. Lactate can become elevated with serious illness and can further be used to help differentiate between anaerobic and aerobic activity. Users partaking in high-intensity interval exercise experienced a greater increase in glucose. The increase corresponded with a greater increase in lactate compared to those participating in moderate-intensity exercise. Accordingly, supplementing glucose data with lactate data can provide insight into intensity of exercise that can be used to predict post-exercise behavior of glucose and corresponding insulin requirements.

In some embodiments, each working electrode has a corresponding counter electrode while in other embodiments multiple working electrodes share a counter electrode. In still other embodiments, two working electrodes share a counter electrode while the third working electrode has a dedicated discrete counter electrode. Furthermore, the various embodiments of working electrodes and counter electrodes can be distributed among separate and discrete substrates. Typically, working electrodes and counter/reference electrodes are formed on a single substrate. However, an electrode design intended for use in the invention allows the complete physical separation of any of the working electrodes and any of the counter/reference electrodes. For example, as is shown in FIGS. 2A and 2B working electrodes for analyte sensors can be formed on A-side 200*a* while counter/reference electrodes are formed on B-side 200*b*. While the various electrodes may be separated on distinct A-side and B-side, in many embodiments the sensor array 101 having the plurality of working electrodes is inserted into the subcutaneous tissue via a single point of insertion. The use of a single insertion point minimizes both patient discomfort associated with insertion and insertion complexity.

Exemplary transducer structures that can be used to for the analyte sensors 101*a* can be found in the following U.S. patent applications: Ser. No. 15/472,194 filed on Mar. 28, 2017; Ser. No. 16/054,649, filed on Aug. 3, 2018; Ser. No. 16/152,727 filed on Oct. 5, 2018; each of which are hereby incorporated by reference for all purposes. Additionally transducer structures can be found in PCT application serial no. PCT/US18/38984 filed on Jun. 22, 2018, which is hereby incorporated by reference for all purposes.

In many embodiments the preferred tissue, to insert the probe containing the analyte sensors 101*a* is subcutaneous tissue. However this should not preclude the use of the probe in other tissues such as, but not limited to skeletal muscle tissue, smooth muscle tissue or even organ tissue. Insertion of an oxygen sensor into any of these types of tissues can provide insight into the microcirculation of the specific tissue, and accordingly, the relative health of the subject.

The specific embodiments described above regarding the analyte sensors 101*a* and the physical sensors 101*b* should not be construed as limiting. In other embodiments the number of analyte sensors that can placed on a single probe is only limited by the physical size of the probe and the willingness of subjects to insert the probe. That is to say, it should be understood that a single probe measuring glucose and any number of additional analytes should be construed as being within the current disclosure. In order to accommodate additional analyte sensing electrodes it may be necessary for some analytes to share a common reference electrode. Furthermore, regarding reference electrodes, while FIG. 2B includes multiple pseudo-reference electrodes, various other embodiments can use various combination of pseudo-reference electrodes, discrete counter electrodes, discrete reference electrodes and various combinations thereof.

Electronics Module

Returning to FIG. 1, the system 100 additionally includes an electronics module 102 that provides power for the sensor array 101 and enables bidirectional communication with other system components such as, but not limited to the external monitor 104, cloud computing systems 106 or mobile devices 128. Enabling the electronics module 102 to perform such tasks are electronic module components such as, but not limited to a communication module 108, a processor 110, memory 112, and a power supply 114 enclosed within an electronics module case. The electronics module 102 includes additional components, however, the specific components found in FIG. 1 warrant discussion regarding operation of the system 100.

In preferred embodiments the power supply 114 provides power to the electronics module 102 and also to the sensor array 101. Batteries, rechargeable or disposable, can be used for the power supply 114. In order to minimize the likelihood of fluid ingress to the electronics module, it may be preferable to use inductive charging for embodiments using rechargeable batteries. Other embodiments use alternatives to batteries such as, but not limited to capacitors, supercapacitors, solar cells, fuel cells and the like. The specific examples provided for the power supply 114 should not be construed as limiting. Rather, the examples provided should be viewed as examples of portable power supplies capable of supplying the electronics module 102 and the sensor array 101 with power for the expected life of the system 100.

In some embodiments the processor 110 is custom circuit such as but not limited to an application-specific integrated circuit (ASIC) or field programmable gate array (FPGA). In other embodiments the processor 110 is a more generic system on chip (SoC) or system in package (SiP). In instances where a SoC or SiP is utilized, communication module 108 and memory 112 can be integrated within the SoC or SiP. In many embodiments the processor is in communication with the sensor array 101 receiving raw signal data from the plurality of working electrodes and other sensors. In some embodiments the processor 110 performs minimal manipulation of the raw data from the working electrodes. Examples of minimal manipulation include, but are not limited to filtering noise and compression. In these embodiments the data from the working electrodes is transmitted to a multitude of external devices via the communication module 108 where processing is completed to detect a physiological state. Alternatively, in other embodiments the processor 110 executes stored instructions to process the sensor data before transmitting processed data that may include detection of a physiological state to any external devices via the communications module 108.

In many embodiments the electronics module 102 is coupled to the sensor array 101 during an insertion process. In most embodiments the electronics module 102 includes a housing that when coupled with the sensor array, seals the combined sensor array 101 and electronics module 102 within a housing that defines an on-body assembly.

Communications and Interconnectivity

In many embodiments the communications module 108 is based on personal area network technology commonly referred to as Bluetooth low energy (BLE) or Bluetooth Smart. In other embodiments, a customized or semi-custom communication standard is utilized. However, one common trait for any communication module 108 is the ability to securely send and receive data between at least a third party device and the electronics communication module 102. The ability to securely transmit either raw or processed data using the communications module 102 enables flexibility that allows the system 100 to be adaptable from a mobile monitor to being an integral component within a hospital ward.

In one embodiment data from the sensor array 101 is sent via the communications module 108 to a cloud computing system 106, also commonly referred to as "the cloud". In still other embodiments data from the sensor array 101 is transmitted via the communications module 108 to an external monitor 104. Clinical settings such as a hospital ward where multiple monitors display a plurality of condition being monitored for a patient could be ideal settings for embodiments where the electronics module 102 transmits to an external monitor 104 or the cloud 106. For example, with the appropriate infrastructure data from the sensor array 101 can be transmitted in real-time to an electronic medical record stored in the cloud 106. Alternatively, in some embodiments data can be transmitted from the external monitor 104 to the cloud 106 where it is stored as part of an electronic medical record.

In still other embodiments, the electronics module 102 transmits data from the sensor array 101 to a mobile device 128 such as, but not limited to a smartphone, a smartwatch, a portable fitness monitor, a tablet, a notebook computer, an ultrabook computer, or an aftermarket or integrated infotainment center for a vehicle. The examples of a mobile device 128 are not intended to be construed as limiting. Rather, the examples are intended to provide guidance regarding the types of devices that can receive and/or transmit data to the electronics module 102. Accordingly, devices that can be viewed as similar to those listed should be considered contemplated by the current disclosure. In embodiments where the mobile device 128 includes a connection to the internet, the mobile device 128 can send data to the cloud 106 where the data can be archived, shared with other devices, be further processed or become data to enable machine learning. Utilizing the data to enable machine learning further enables data-driven improvements such as development of algorithms that are patient specific or algorithms that are applied universally across all patients. For example, depending on how much information is provided with the data provided for machine learning, patient specific algorithms can include, but are not limited to factors such as age, race, weight, and pre-existing conditions. Processing the plurality of data streams available from the analyte sensors and physical sensors can enable highly personalized models of an individual's unique diabetes that can enable improved closed loop systems or improved dosing of manually administered multiple daily injections. Similarly, regardless of patient specific information, all data processed via machine learning can be utilized to create new and improve existing predictive algorithms with the goal being improved outcomes for all patients.

Even with embodiments where additional processing is handled on either an external monitor 104 or the cloud 106, memory 112 can be used to store data from the sensor array 101 on the electronics module 102. Using the memory 112 to store data from the sensor array 101 can ensure sensor data is not lost if there are connectivity interruptions between the electronics module 102 and the external monitor 104, the cloud 106, or a mobile device 128. The memory 112 can further be used to store program instructions for the processor, or to store values for variables used by the processor 110 to detect a physiological state.

In many embodiments the electronics module 102 is removably coupled with the sensor array 101. With these embodiments, the electronics module 102 is capable of being reused after the sensor array 101 is deemed consumed or depleted. In other embodiments, a permanent coupling is achieved after an initial coupling between the electronic module 102 and the sensor array 101. In these embodiments, the electronics module 102 is considered disposable and is intended to be discarded after the sensor array 101 is deemed consumed. Alternatively, to reduce environmental impact, select portions of the electronics module, such as, but not limited to the power supply 114 and communications module 108 are recyclable. In many embodiments, initially coupling the electronics module 102 to the sensor array 101 provides power to the electrodes and initiates the program instructions stored in either the processor 110 or the memory 112.

In many of these embodiments, the electronics module includes a feedback device 113. The feedback device 113 provides feedback regarding the status of the combined electronics module 102 and sensor array 101. For example, in some embodiments the feedback device 113 is a single or a plurality of multi colored LED that blinks a first color and/or first pattern when the system is functioning with design parameters and a second color and/or second pattern if there is an error within the system. In other embodiments, the LED is a single color that uses different frequency of blinks to convey status of the system. In still other embodiments, the feedback module includes a vibration device similar those used in mobile phones to convey status of the system. In still other embodiments, a piezo or other audible sound emitting device is used as the feedback device 113.

The external monitor 104 may include some components not found in the electronics module 102, such as a graphic user interface (GUI) 122 and a display 124. Other components of the external monitor 104, such as a communication module 116, a processor 118, a memory 120 and a power supply 126 may seem duplicative of components in the electronics module 102, but may have different or improved capabilities or functionality. For example, while the power supply 114 of the electronics module 102 may be a battery, the power supply 126 for the external monitor 104 may include an AC power supply that is supplemented with a rechargeable battery to enable the external monitor 104 to operate seamlessly between being plugged into a wall socket and being moved throughout a hospital until it can be eventually be plugged back into a wall socket.

For purposes of this invention, the GUI 122 further includes human interface devices that enable interaction with the GUI 122 such as but not limited to virtual or physical keyboards, touchscreens, joysticks, control pads and the like. Accordingly, use of the GUI 122 in conjunction with the display 124 enables user input to the system 100 and further allows selection or customization of what is shown on the display 124. The GUI 122 in conjunction with the communication module 116 and the communication module 108 further enables settings on the electronics module 102 to be manipulated or adjusted to optimize output from the system 100. Similarly, the GUI 122 enables user input to the processor 118 or the memory 120 to enable input and adjust settings that are applied to data from the sensor array 101 to detect a physiological state.

The system further optionally includes a mobile device 128 having a user interface, such as, but not limited to a smartphone, a mobile phone, a smartwatch, a laptop, an ultrabook, a tablet computing device, a pager, and the like. The mobile device 128 is configured to receive data from the electronics module 102 via at least one of the cloud 106, the external monitor 104, or the electronics module 102 itself. In many embodiments the mobile device 128 is in bidirectional communication with the electronics module 102 that enables input via the user interface of the mobile device 128 to be transmitted to the electronic module 102. This enables a user of the mobile device 128 to manipulate, configure, or program settings on the electronics module 102. In some embodiments, bidirectional communications enables processing of data from the sensor array 101 on the mobile device 128. Additionally, in embodiments where the mobile device 128 includes a display, real time data and trends derived from the data is shown on the mobile device 128. In embodiments where the mobile device 128 includes at least one of an audible, tactile and visual alarm, the mobile device 128 can be used to update users of the mobile device 128 of the status of a patient wearing the sensor array 101. The status of the user includes, but is not limited to whether the system 100 is functioning properly, faults within the system 100, or real time measurements from the sensor array 101.

Another optional component within the system 100 is the cloud 106. Generally, the cloud 106 is considered a type of cloud computing that can be generalized as internet based computing that provides on demand shared computing processing resources and data to computer and other internet connected devices. In some embodiments the cloud 106 receives data from the electronics module 102 directly. In other embodiments data from the electronics module is transmitted to the mobile device 128 before being transmitted to the cloud 106. In still other embodiments, the cloud 106 receives data from the electronics module 102 via the external monitor 104. In still other embodiments, various permutations of communications initiated by the electronics module and transmitted between the external monitor 104 and the mobile device 128 results in data being transmitted to the cloud 106.

Data received by the cloud 106 may have already been processed by an intermediary device or can be processed on the cloud 106 and transmitted back to the intermediary device. In some embodiments, the cloud 106 contains electronic medical records and data from the sensor array 101 is automatically uploaded to the electronic medical records. With real time data being uploaded to the cloud, it becomes possible to apply machine learning which can further enable automatic or semi-automatic adjustments to the electronics module 102. Automatic updating would result in changes to the programming of the electronics module without human intervention whereas semi-automatic updating would require someone to confirm changes to the programming of the electronics module 102. In one example, the cloud 106 enables examination of medical history such as pre-existing conditions and family history and machine learning can suggest or set customized thresholds and sensor sampling rates based on previous data from patients with similar conditions and data. In another example, the cloud 106 uses historical patterns of physiological state to better detect and predict future such states based on the sensor data.

The previously discussed components or elements within the system 100 are intended to be exemplary rather than limiting. As the system is intended to be flexible components are able to be added and removed based on immediate needs. This includes enabling or disabling system components within one environment while enabling or disabling the same system components at a later point.

Detecting a Physiological State—Relationships Between Analytes

Figure 3:
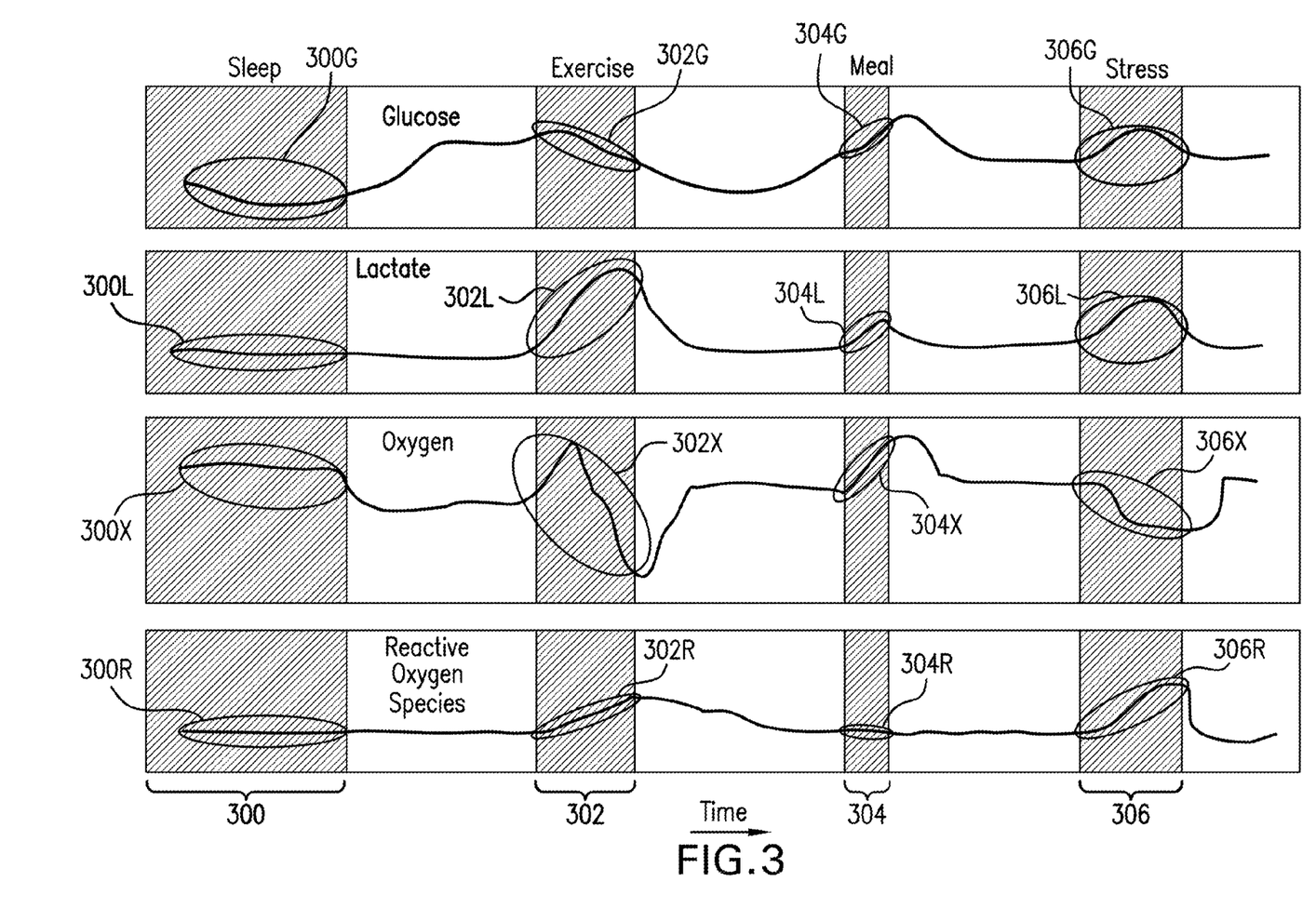
FIG. 3 is an exemplary illustration of real-time glucose, lactate, oxygen, and reactive oxygen species data or various physiological states such as sleep, exercise, a meal and stress.

FIG. 3 is an exemplary illustration of real-time glucose, lactate, oxygen, and ROS data or various physiological states such as sleep 300, exercise 302, a meal 304 and stress 306, in accordance with embodiments of the present invention. Note that the durations of the various physiological states are not intended to be to scale. Rather the physiological states and the exemplary "data" within the duration of the physiological condition is intended to illustrate exemplary trends and rates of change. In practice, it may be necessary to calibrate detection algorithms using days, weeks, or even months of individual patient data. Note that though the detected physiological states are shown as independent episodes, physiological states are not necessarily exclusive in time—it is possible that multiple physiological states may be detected simultaneously.

The current invention is directed toward using a single probe to measure glucose and at least one other analyte. Data obtained via the multi-analyte single probe can be used to refine personalized treatment or therapy using multiple daily injections or other non-insulin pump based therapies. Alternatively, multi-analyte single probe data can be used to refine artificial pancreas control algorithms. Specifically, monitoring continuous data from glucose and the second analyte providing insight to glucose and insulin dynamics along with contextual information to support changes to automated insulin delivery in response to, or in anticipation of, glucose changes. In some embodiments combinations of analyte sensor data (glucose plus at least one additional analyte) are used to initially detect a physiological state. In other embodiments, physiological states are initially detected using a combination of analyte sensor data and physical sensor data such as, but not limited to accelerometers, temperature sensors, hydration sensors, timers, ECG and the like. In these embodiments the physical sensors are installed or enabled via hardware and/or software within the electronics package associated with the analyte sensors. In still other embodiments, initial detection of a physiological state is determined based on physical sensor data. Regardless of how initial detection of the physiological state is determined, subsequently acquired data from either analyte sensors or physical sensors can be used to confirm or reject the initial detection.

In one embodiment glucose and tissue oxygen are the analytes being monitored. Accordingly, in FIG. 3, sleep glucose values 300G and sleep lactate 300L are actively being acquired starting from the left to the right. Initially 300G is in a shallow decline that eventually levels out with even a slight increase toward the end of the sleep state. Similarly, sleep lactate 300L is illustrated as a relatively flat line. Accordingly, in some embodiments prolonged periods of steady lactate data in conjunction with decreasing to leveling glucose data can result in an initial detection of a sleep state. In embodiments where analyte sensors are supplemented by physical sensors, exemplary physical data acquired by accelerometers, thermometers, elapsed time, and ECG systems can confirm or refute the detection of a sleep state by the analyte sensor data. In preferred embodiments, analyte sensor data and physical sensor data are examined simultaneously for an initial detection of a sleep state and continued analysis of analyte and sensor data is used to confirm or refute the initial detection. In standalone MCGM applications detection and confirmation of the detection can be written into memory for subsequent review by the patient or their physician. In AP applications, confirmation of detection can be determined by calculating a confidence score of physiological state. An AP application can be programmed to automatically perform modifications to basal or bolus therapy based on physiological states having a confidence score meeting or exceeding a threshold value.

Examining real-time glucose and lactate data can automatically detect a second physiological state such as exercise 302. Exercise glucose 302G and exercise lactate 303L are exemplary and are not intended to be indicative of any particular individual or group of individuals. What is to be noted for each analyte is the combination of absolute change and rate of change. As expected, as exercise is performed glucose levels will decrease. Similarly, during aerobic exercise lactate levels may gradually increase until the exertion becomes anaerobic, where lactate levels may increase at a more rapid rate.

Meal consumption can also be identified by examining real-time glucose and lactate data. Meal glucose 304G and meal lactate 304L each show increases during, or shortly after a meal. It may be very beneficial to supplement analyte sensor data with time when attempting to detect a meal state. Specifically, it may be very beneficial to include historical meal times within an algorithm to assist in distinguishing between a meal state and an exercise state. While the meal glucose 304G data and meal lactate 304L data is purely exemplary, rates of change and absolute value changes of each analyte across various meals and roughly the same time can help detect a meal state with increasing confidence.

Stress is another physiological state that may be detected using a combination of analyte and physical sensors. Stress glucose 306G and stress lactate 306L are exemplary illustrations of data obtained during a period of stress. In the exemplary data both glucose and lactate increase and decrease a relatively modest amount. Again, the exemplary data can be supplemented by physical sensor data that can be used to increase confidence in detecting stress The simplest embodiments combine glucose with another analyte such as a lactate, discussed above, or oxygen or ROS. In some embodiments glucose and two additional analytes are measured while in still other embodiments, glucose and three other analytes are measured. Factors such a the physical size of the sensor, transducer size, and capabilities of the electronics package limit the number of analytes that can be concurrently measured with glucose.

FIG. 3 includes exemplary illustrations of sleep oxygen 300X, exercise oxygen 302X, meal oxygen 304X and stress oxygen 306X can be used in conjunction with glucose or other analytes to help detect the various physiological states. Oxygen changes in response to exercise and meals and can enable more reliable detection of sleep than accelerometers. Fortunately, because accelerometers can be included as physical sensors, in some embodiments sleep oxygen 300X and be detected via either analyte or physical sensors and further confirmed using either or both analyte or physical sensors.

FIG. 3 further includes exemplary illustrations of sleep ROS 300R, exercise ROS 302R, meal ROS 304R and stress ROS 306R. Concentration of ROS in the body provide insight into oxidative stress. Additionally, oxidative stress can impact the timing of postprandial glucose excursions, causing a delay in glucose decrease after a meal. Because of the involvement of oxidative stress in many diabetes related complications, concentration of ROSS can also provide information on the risk of developing secondary diseases.

The analytes illustrated and discussed regarding FIG. 3 are exemplary and should not be construed as limiting. In other embodiments additional analytes associated with diabetes, diabetes related complications, and secondary diseases may be monitored in conjunction with glucose. In some embodiments, glucose and multiple analytes are monitored to detect a physiological state. In many of those embodiments every analyte is measured while the sensor is implanted. In other embodiments, select analytes are measured only after a physiological condition is detected or another threshold triggers measurement of the select analyte. The rationale for selectively measuring specific analytes can be one of saving power, reducing potential crosstalk among the various working electrodes, reducing computational requirements, controlling memory usage and the like.

Figure 4:
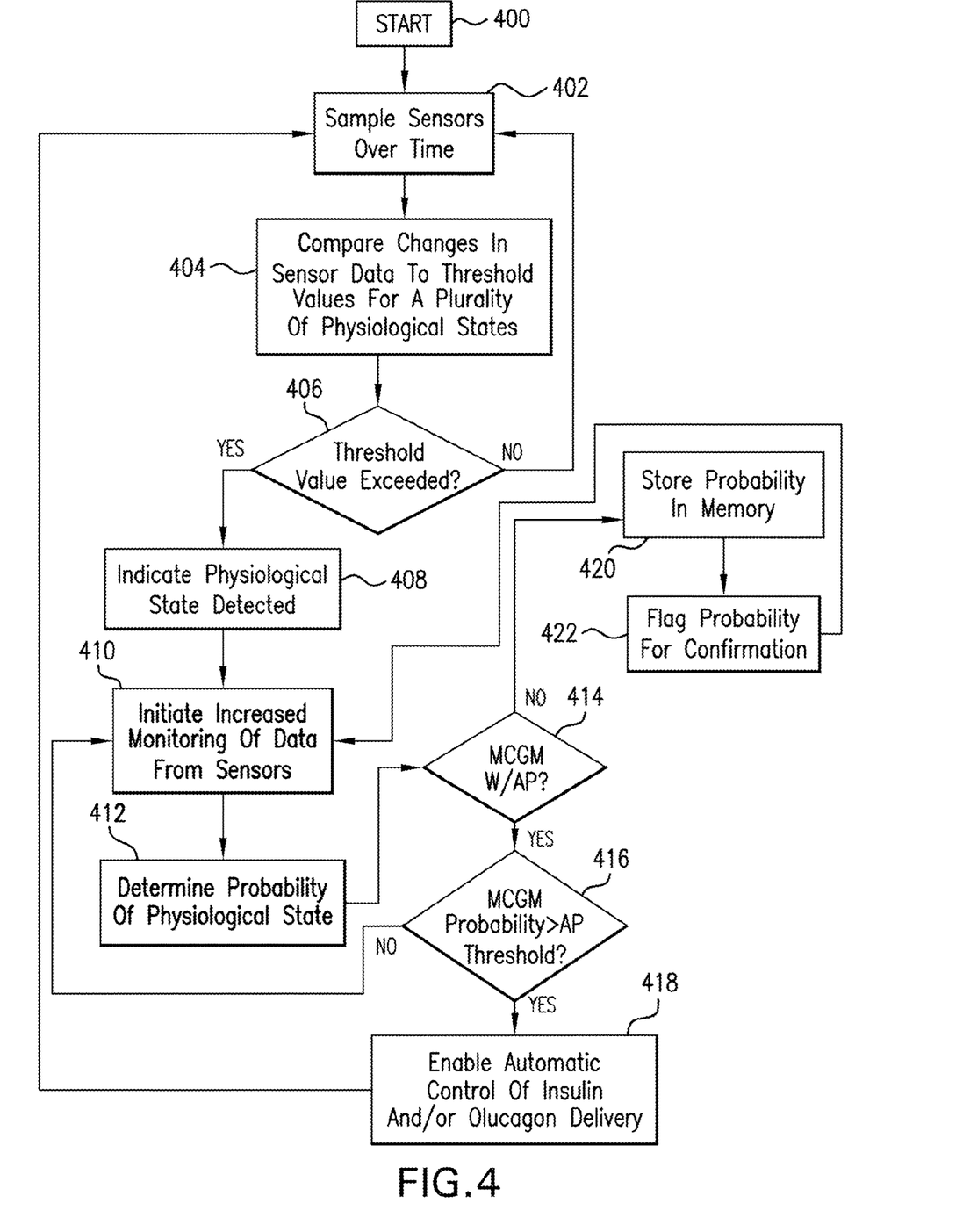
FIG. 4 is an exemplary flowchart illustrating one embodiment of detecting a physiological condition.

FIG. 4 is an exemplary flowchart illustrating one embodiment of detecting a physiological condition, in accordance with various embodiments of the present invention. The flowchart begins with START operation 400 that could be viewed as being roughly equivalent to having inserted, powered, and properly hydrated, or run-in, the analyte sensors. Additionally, in some embodiments the physical sensors are similarly ready to produce meaningful data. Operation 402 begins sampling and storing data from both the analyte sensors and physical sensors. Operation 404 compares changes in data streams from the sensors to threshold values for a plurality of physiological states. Operation 404 is where data streams from the analyte and physical sensors are processed to look for combinations of absolute changes or rates of change that exceed a threshold value indicative of a known physiological state such as, but not limited to, sleep, eating a meal, exercise or stress.

Operation 406 compares whether any threshold values indicative of a physiological state have been exceeded. If no threshold values have been exceeded, the flowchart returns to operation 402. If a threshold value has been exceeded, the flowchart proceeds to operation 408 that identifies which physiological state has been detected. Operation 410 initiates increased monitoring of data from the sensors. With a physiological state detected, the system can begin interrogating analyte and physical sensors to obtain data to either confirm or refute the initial detection. Operation 412 determines, or calculates a probability of the physiological state based on the increased monitoring from the sensors. Operation 414 compares whether the sensor data is associated with an artificial pancreas system. If no artificial pancreas system is associated, operation 420 stores the probability in memory while subsequent operation 422 flags the probability data for confirmation. In many embodiments confirmed data can be processed via machine learning or predictive analytics tools to create or modify individual or multi-patient models that can be subsequently used to detect physiological states. If an artificial pancreas system is associated, operation 416 compares the probability of a physiological condition to a minimum probability threshold for the artificial pancreas system. If the probability is greater than the minimum probability threshold operation 418 enable automatic control of insulin or glucagon delivery from the artificial pancreas system. In many embodiments, detection of a physiological state alone does not necessarily require augmentation of insulin or glucagon delivery. Rather, the detected physiological state becomes another variable in determining whether modifications to insulin or glucagon may be necessary to control a patient's glucose. If the probability of a physiological state does not meet the artificial pancreas minimum requirement the flowchart returns to either operation 402 or 410.

The operations described above are intended to detect a single physiological state. However, in preferred embodiments, multiple physiological states can be detected and their respective probabilities can be parsed simultaneously. Physiological conditions such as stress and illness can occur simultaneously with states like exercising, ingesting a meal and sleeping. Accordingly, the system is configured to identify at least one or more physiological state from a plurality of physiological states. The operations discussed above are intended to be exemplary. In many embodiments additional operations can be performed before, between and after the exemplary operations presented above. Alternatively, in other embodiments, fewer operations can be performed to detect a physiological state. In still other embodiments, where possible, discontiguous operations can be combined or have other operations performed before or after the exemplary operations.

Throughout the description the system has been described as sensors associated with and electronics package that enable communication to additional devices. However, in some embodiments, the system 100 (FIG. 1) can be incorporated into a network of sensors that includes various combinations of multiple sensors (ranging from non-invasive, minimally invasive to invasive) that are optionally interconnected via an on-body network. The networked sensors can be similar to those described in U.S. patent application Ser. No. 15/417,055 filed on Jan. 26, 2017 and Ser. No. 16/054,649, filed on Aug. 3, 2018. Alternative embodiments utilize a variety of other sensors capable of measuring a variety of other conditions. Each different sensor within the networked sensors can be operated continuously or alternatively, periodically or episodically to gain additional insight into physiological states and conditions.

Accordingly, while the description above refers to particular embodiments of the invention, it will be understood that many modifications may be made without departing from the spirit thereof. In particular, while many embodiments are directed toward specific combinations of analytes and physical sensor data, it should be understood that where possible, each embodiment is capable of being combined with each and every other embodiment. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

The invention claimed is:

1. A system to automatically detect at least one physiological state, comprising:
   a single probe having an A-side and a B-side for insertion within a subject having an analyte sensor array for continuous monitoring of at least glucose and a second analyte, the single probe having working electrodes on the A-side of the single probe and a pseudo-reference electrode on the B-side of the single probe that is opposite the A-side, the single probe further having the working electrodes being patterned on a first substrate and the pseudo-reference electrode being patterned on a second substrate; and
   an electronics module having a power supply, a processor, memory and a bi-directional communications module, the electronics module configured to couple with the analyte sensor array, the power supply powering the analyte sensor array and the processor being in communication with the analyte sensor array, the processor analyzing glucose and the second analyte to detect a first physiological state from a plurality of physiological states.

2. The system of claim 1, wherein detecting the first physiological state is based on a combination of absolute change and rate of change of glucose and absolute change and rate of change of the second analyte.

3. The system of claim 2, wherein the second analyte is tissue oxygen.

4. The system of claim 3, wherein the plurality of physiological states include exercise, a postprandial state, sleep and stress.

5. The system of claim 3, wherein the analyte sensor array on the single probe is further configured to monitor a third analyte, the third analyte being one of lactate, reactive oxygen species, and ketones.

6. The system of claim 5, wherein the processor analyzes the third analyte with respect to glucose and tissue oxygen to further enable detection of the first physiological state and a second physiological state.

7. The system of claim 6, wherein the electronics module further includes at least one physical sensor, data from the at least one physical sensor being analyzed by the processor and used in conjunction with data monitored from at least one of glucose, tissue oxygen or the third analyte to detect or confirm either the first or second physiological state.

8. The system of claim 2, wherein the second analyte is lactate.

9. The system of claim 8, wherein the first physiological state is one of illness, or exercise that is either anaerobic or aerobic.

10. The system of claim 8, wherein the analyte sensor array on the single probe is further configured to monitor a third analyte, the third analyte being one of tissue oxygen, reactive oxygen species and ketones.

11. The system of claim 10, wherein the processor analyzes the third analyte with respect to glucose and lactate to further enable detection of the first physiological state and a second physiological state.

12. The system of claim 2, wherein the second analyte is reactive oxygen species.

13. The system of claim 12, where the first physiological state is one of stress and illness.

14. The system of claim 12, wherein the analyte sensor array on the single probe is further configured to monitor a third analyte, the third analyte being one of tissue oxygen, lactate, and ketones.

15. The system of claim 14, wherein the processor analyzes the third analyte with respect to glucose and reactive oxygen species to further enable detection of a second physiological state.

* * * * *